(12) United States Patent
Taneichi et al.

(10) Patent No.: US 7,303,808 B2
(45) Date of Patent: Dec. 4, 2007

(54) BULKY SHEET MATERIAL HAVING THREE-DIMENSIONAL PROTRUSIONS

(75) Inventors: Shoichi Taneichi, Haga-gun (JP);
Manabu Kaneta, Haga-gun (JP);
Yasuhiro Komori, Haga-gun (JP);
Takanobu Miyamoto, Haga-gun (JP);
Wataru Saka, Haga-gun (JP);
Yoshihiro Sakai, Haga-gun (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 09/973,802

(22) Filed: Oct. 11, 2001

(65) Prior Publication Data

US 2002/0068150 A1 Jun. 6, 2002

(30) Foreign Application Priority Data

Oct. 12, 2000 (JP) ............................. 2000-311415

(51) Int. Cl.
*B32B 3/10* (2006.01)

(52) U.S. Cl. .................. 428/198; 428/114; 428/131; 428/137; 428/138; 428/170; 428/171; 428/172; 428/152; 428/156; 442/352; 442/328; 442/353; 442/358; 442/359; 442/360; 442/361; 442/381; 604/378; 604/380; 604/383; 604/385.101; 604/385.01

(58) Field of Classification Search ............... 428/198, 428/114, 131, 137, 138, 170, 171, 172, 156, 428/152; 442/352, 328, 353, 358, 359, 360, 442/361, 381, 383; 604/378, 380, 385.101, 604/385.01

See application file for complete search history.

(56) References Cited

U.S. PATENT DOCUMENTS

| 4,041,203 A | 8/1977 | Brock et al. | |
|---|---|---|---|
| 4,323,068 A | 4/1982 | Aziz | |
| 4,551,378 A * | 11/1985 | Carey, Jr. | 428/198 |
| 4,720,415 A * | 1/1988 | Vander Wielen et al. | 156/163 |
| 4,935,022 A | 6/1990 | Lash et al. | |
| 5,143,779 A | 9/1992 | Newkirk et al. | |
| 5,229,191 A | 7/1993 | Austin | |
| 5,348,547 A | 9/1994 | Payne et al. | |
| 5,399,174 A | 3/1995 | Yeo et al. | |
| 5,491,016 A * | 2/1996 | Kaiser et al. | 428/198 |
| 5,536,555 A * | 7/1996 | Zelazoski et al. | 128/849 |
| 5,591,149 A | 1/1997 | Cree et al. | |
| 5,612,118 A * | 3/1997 | Schleinz et al. | 101/131 |
| 5,624,427 A * | 4/1997 | Bergman et al. | 604/391 |

(Continued)

FOREIGN PATENT DOCUMENTS

CN 1178101 A 4/1998

(Continued)

*Primary Examiner*—William P Watkins, III
(74) *Attorney, Agent, or Firm*—Birch, Stewart, Kolasch & Birch, LLP (57) ABSTRACT

A bulky sheet material having three-dimensional protrusions 10 is disclosed. The sheet material comprises a first layer 1 and a second layer 2 adjacent to the first layer 1. The first layer 1 and the second layer 2 is partly joined together at joints 3 in a prescribed pattern. The first layer 1 has a number of raised portions which are located among the joints 3. The second layer 2 comprises a material which exhibits elastomeric behavior. The bulky sheet material 10 exhibits elastomeric behavior as a whole and breathability.

15 Claims, 3 Drawing Sheets

U.S. PATENT DOCUMENTS

| | | | |
|---|---|---|---|
| 5,817,394 A | 10/1998 | Alikhan et al. | |
| 5,989,688 A | 11/1999 | Barge et al. | |
| 6,362,391 B1 | 3/2002 | Mizutani et al. | |
| 6,673,418 B1 | 1/2004 | DeOlivera et al. | |
| 2002/0068150 A1 | 6/2002 | Taneichi et al. | |
| 2003/0134094 A1* | 7/2003 | Zafiroglu et al. | 428/198 |
| 2003/0162460 A1* | 8/2003 | Saka et al. | 442/394 |

FOREIGN PATENT DOCUMENTS

| | | |
|---|---|---|
| EP | 0327317 A2 | 8/1989 |
| EP | 359501 A2 | 3/1990 |
| EP | 0604731 A1 | 7/1994 |
| EP | 0841156 A1 | 5/1998 |
| EP | 1338262 A1 | 8/2003 |
| GB | 2288412 A | 10/1995 |
| JP | 51-146584 A | 12/1976 |
| JP | 61-124667 A | 6/1986 |
| JP | 62-141167 | 6/1987 |
| JP | 63-296936 A | 12/1988 |
| JP | 63-309657 A | 12/1988 |
| JP | 2-133641 A | 5/1990 |
| JP | 02-300365 A | 12/1990 |
| JP | 04-312431 A | 11/1992 |
| JP | 5-25763 A | 2/1993 |
| JP | 6017356 A | 1/1994 |
| JP | 6-128853 | 5/1994 |
| JP | 7-232409 A | 9/1995 |
| JP | 8-3850 A | 1/1996 |
| JP | 9-003755 | 1/1997 |
| JP | 9-111631 | 4/1997 |
| JP | 09-117982 A | 5/1997 |
| JP | 10-80445 A | 3/1998 |
| JP | 2000-135239 A | 5/2000 |
| JP | 2000-210334 A | 8/2000 |
| JP | 3131557 B2 | 11/2000 |
| JP | 2001-37805 A | 2/2001 |
| JP | 3181195 B2 | 4/2001 |
| JP | 2001-140158 A | 5/2001 |
| WO | WO-98/24389 A1 | 6/1998 |
| WO | WO-00/35503 A1 | 6/2000 |

* cited by examiner

BULKY SHEET MATERIAL HAVING THREE-DIMENSIONAL PROTRUSIONS

BACKGROUND OF THE INVENTION

The present invention relates to a bulky sheet material having a large number of three-dimensional protrusions and showing an elastomeric behavior as a whole and breathability.

The subject in developing absorbent articles such as sanitary napkins and disposable diapers is fulfillment of requirements that: absorbent articles should retain wastes discharged from the body such as menstrual blood and urine without leakage; brought into direct contact with a wearer's skin, they should not give a wearer discomfort; and they should not cause a rash due to overhydration and the like.

Conventional absorbent articles are not easily deformable even with pressure applied while worn and therefore give a wearer discomfort. They are incapable of following the wearer's contour or movement, tending to result in leakage. The wearer's side having a smooth surface and being made of a relatively high-density material, they are liable to cause a skin rash due to overhydration.

To eliminate these inconveniences, JP-A-6-128853 proposes using wrinkly nonwoven fabric as a topsheet of an absorbent article. The wrinkly nonwoven fabric disclosed exhibits insufficient recovery when extended in the planar direction. Therefore, where used as a topsheet, etc. of an absorbent article, it has insufficient conformability to the movement of a wearer, tending to result in a leak. Besides, the wrinkly nonwoven fabric has insufficient compressive deformability when compressed in its thickness direction. Therefore, when it is deformed by compression while worn, it is liable to come into intimate contact with the wearer's body to give discomfort.

JP-A-62-141167 teaches a method of making a composite sheet having an uneven structure, which comprises superposing nonwoven sheets having different shrinkages on each other and joining them in parts. Similarly to the aforementioned wrinkly nonwoven fabric, the composite sheet is unsatisfactory in recovery from extension in the planar direction and deformability when compressed in the thickness direction. Moreover, because knitted fabric is used as a sheet having a smaller thermal shrinkage, the composite sheet as a whole has a high density, which can cause overhydration.

JP-A-9-111631 discloses a wrinkled nonwoven fabric comprising a first fibrous layer and a second fibrous layer provided on one side of the first fibrous layer in which the first fibrous layer contains thermally shrinkable fibers and the second fibrous layer contains thermally fusible fibers. Two fibrous layers are combined in the thickness direction at the thermally bonded portions of linear shape. The thermally bonded portions form recessed regions and the portions between the thermally bonded portions form raised regions. In addition, the second fibrous layers has a great number of wrinkles of linear shape. This wrinkled nonwoven fabric, however, is unsatisfactory in recovery from extension in the planar direction and deformability when compressed in the thickness direction.

SUMMARY OF THE INVENTION

An object of the present invention is to provide a bulky sheet material having three-dimensional protrusions which exhibits sufficient recovery from extension in the planar direction and sufficient compressive deformability in the thickness direction and has a relatively small density as a whole.

The present invention accomplishes the above object by providing a bulky sheet material having three-dimensional protrusions comprising a first layer and a second layer adjacent to the first layer, said first layer and said second layer being partly joined together at joints in a prescribed pattern, said first layer having a number of raised portions which are located among said joints, said second layer comprising a material which exhibits elastomeric behavior, and said bulky sheet material exhibiting elastomeric behavior as a whole and breathability.

The present invention also provides a preferred method of producing the above-described bulky sheet material which comprises the steps of:

carding fibers by a carding machine to form a carded web that is a first layer, superposing the first layer and a separately prepared second layer on each other, joining the first layer and the second layer in parts forming a prescribed pattern, and heat-treating the joined sheets at or above a temperature at which the fiber constituting the second layer starts thermal shrinkage thereby to shrink the second layer.

BRIEF DESCRIPTION OF THE DRAWINGS

The present invention will be more particularly described with reference to the accompanying drawings, in which.

DETAILED DESCRIPTION OF TEE PREFERRED EMBODIMENTS

Figure 1:
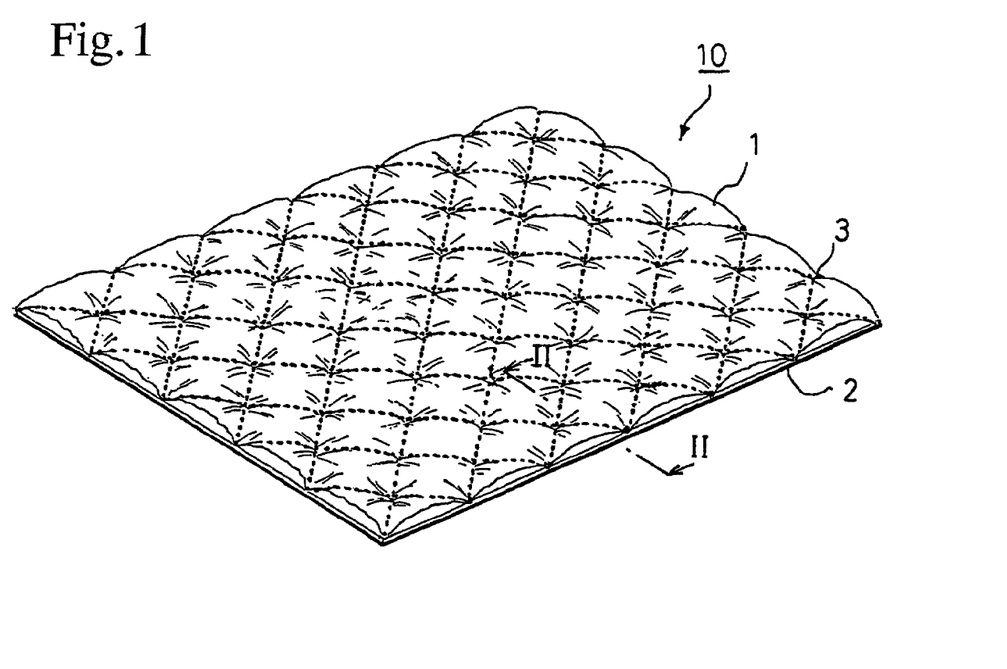
FIG. 1 is a perspective of a bulky sheet material according to an embodiment of the present invention.
Figure 2:
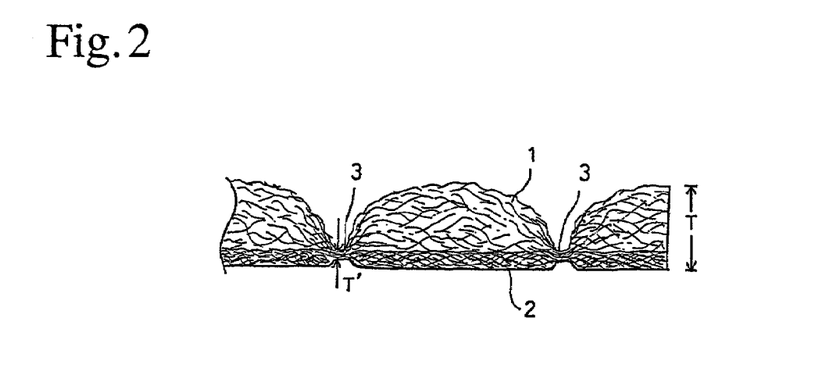
FIG. 2 is a cross-section taken along line II-II of FIG. 1.

The present invention will be described based on preferred embodiments thereof with reference to the accompanying drawings. FIG. 1 is a perspective of a bulky sheet material having three-dimensional protrusions according an embodiment of the present invention. FIG. 2 is a cross-sectional view of FIG. 1 taken along II-II line.

The bulky sheet material 10 shown in FIG. 1 has a first layer 1 and a second layer 2 adjacent to the first layer 1. The first layer 1 and the second layer 2 are partly joined at a large number of joints 3. In this embodiment, the joints 3 each have a circular plane view and are discontinuously arranged in a rhombic lattice pattern. The joints 3 have a smaller thickness and a higher density than other parts of the bulky sheet material 10.

The joints 3 are formed by various joining means, such as heat embossing, ultrasonic embossing or bonding with an adhesive. While the individual joints 3 in this embodiment are circles, they can be ellipses, triangles, rectangles or combinations thereof, or they can be formed continuously to make straight lines or curves.

The area ratio of the joints 3 to the entire surface of the bulky sheet material 10 (the area ratio of the joints 3 per unit area of the bulky sheet material 10) is preferably 3 to 50%, still preferably 5 to 35%, which depends on the end use of the bulky sheet material 10, for obtaining sufficient bonding strength between the first layer and the second layer while ensuring sufficient height of raised portions, namely, protrusions to produce bulkiness.

In the present embodiment, the first layer 1 is an aggregate of fibers, and the second layer 2 is an aggregate of fibers different from those making up the first layer I in kind and/or composition.

The sheet material 10 has a great number of surrounded portions which are surrounded by the joints 3 arranged in a pattern. Thus, there are formed in the first layer 1 a great number of raised or protruded portions surrounded by the joints 3 as shown in FIG. 2. Such a three-dimensional configuration is one of the features of the bulky sheet material according to the present invention. In this particular embodiment, the protrusions are domes filled with fibers constituting the first layer. According to a specific method hereinafter described, it is possible to have the fibers making the outer surface of every dome orientated along the contour of the dome. On the other hand, the second layer 2 has an almost flat surface in the portions other than the joints 3 as shown in FIG. 2. Macroscopically, the bulky sheet material 10 is flat on its second layer side and has a large number of protrusions on its first layer side.

Figure 3A:
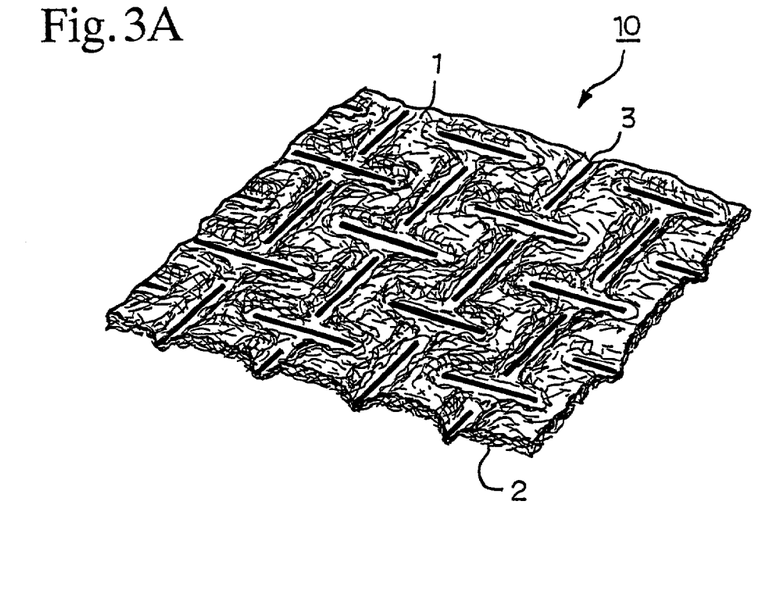
FIG. 3A is a perspective of a bulky sheet material according to another embodiment of the present invention.

The three-dimensional configuration of the protrusions is not limited to domes as shown in FIGS. 1 and 2 and includes, for example, wrinkles shown in FIG. 3A. The wrinkly surface shown in FIG. 3A can be obtained by, for example, forming joints 3 in the pattern described in FIG. 3B.

Figure 4:
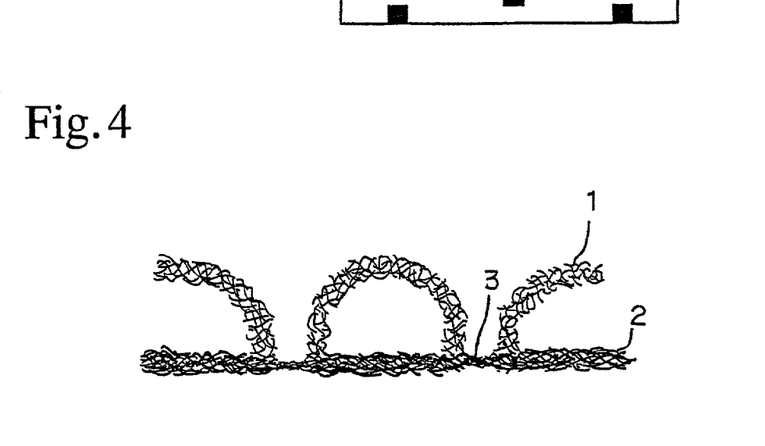
FIG. 4 is a cross-section of a bulky sheet material according to still another embodiment of the present invention, which corresponds to FIG. 2.

Instead of being filled with fibers, the individual domes may be hollow as illustrated in FIG. 4. In this case, the fiber aggregate as the first layer 1 is nonwoven fabric or knitted fabric.

Whatever configuration the protrusions may have, the bulky sheet material 10 feels sufficiently bulky as long as the ratio of thickness of the sheet material T at the protrusions to thickness of the sheet material T' at the joints 3 (T/T', see FIG. 2) is 2 or greater. The upper limit of T/T' is about 6, which is decided according to the shape retention of the protrusions and the basis weight of the bulky sheet material 10.

The thicknesses T and T' are measured as follows. The bulky sheet material 10 is cut into a square piece of 50 cm by 50 cm. A plate weighing 10 g and slightly larger than the cut piece is put on the cut piece, and the thickness of the piece in this state, which is taken as the thickness at the protrusions (T), is measured with, for example, a dial gauge or a laser displacement meter. The thickness T thus measured equals to a "thickness under a pressure of 0.4 cN/cm$^2$" as hereinafter referred to.

On the other hand, the thickness T' at the joint 3 is measured while a pressure of 10 to 40 N/cm$^2$ is applied to the joint 3 with a feeler equal to or smaller than the joint 3 in size. Measurement can be made with the same instrument as used for the measurement of thickness T.

Another feature of the bulky sheet material 10 according to the present invention resides in that it has a low-density structure to show sufficient compressive deformability when compressed in the thickness direction. More specifically, it is generally preferred, while depending on the final use, for the bulky sheet material 10 to have an apparent density of 5 to 50 kg/r$^3$, particularly 10 to 30 kg/m$^3$, under a pressure of 0.4 cN/cm$^2$. The bulky sheet material 10 having such an apparent density feels bulky and exhibits improved compressive deformability which leads to improved flexibility. It is also preferred for the bulky sheet material 10 to have an apparent density of 20 to 130 kg/m$^3$, particularly 30 to 120 kg/m$^3$, under a pressure of 34.2 cN/cm$^2$. The bulky sheet material 10 having such an apparent density has sufficient strength to exhibit improved three-dimensional shape retention and to secure sufficient breathability. To secure sufficient breathability is especially effective to prevent an overhydration-induced skin rash when the bulky sheet material 10 is used as an element constituting an absorbent article. The pressure of 0.4 cN/cm$^2$ is almost equal to the pressure applied to an absorbent article while fitted to a wearer's body, and the pressure of 34.2 cN/cm$^2$ is almost equal to the body pressure imposed to an absorbent article while worn.

The apparent density of the bulky sheet material 10 under a pressure of 0.4 cN/cm$^2$ and that under a pressure of 34.2 cN/cm$^2$ are obtained by dividing the basis weight by the thickness under the respective pressures hereinafter described.

While varying according to the use, the thickness of the bulky sheet material 10 is preferably 1.5 to 10 mm, particularly 2 to 6 mm, under a pressure of 0.4 cN/cm$^2$ and 1 to 5 mm, particularly 1.5 to 3 mm, under a pressure of 34.2 cN/cm$^2$ from the standpoint of bulkiness and compressive deformability.

The thickness under a pressure of 0.4 cN/cm$^2$ (hereinafter referred to as T1) is measured as follows. The bulky sheet material 10 is cut into a square piece of 50 mm by 50 mm. A plate weighing 10 g and slightly larger than the cut piece is put on the measuring stage. The position of the upper side of the plate in this state is referred to as the original position A. Then the plate is removed from the measuring stage, and the cut piece of the sheet material is put on the measuring stage, followed by putting again the plate on the cut piece. The position of the upper side of the plate in this state is referred to as the position B. The thickness of the sheet material 10 is obtained by the difference of the position A and position B. While the measurement is made with a laser displacement meter (CCD LASER DISPLACEMENT SENSOR LK-80 available from KEYENCE CORPORATION), a dial gauge may be used. Where the dial gauge is used, the pressure due to the plate and the dial gauge should be controlled so as to apply the total pressure of 0.4 cN/cm$^2$ to the cut piece.

The thickness under a pressure of 34.2 cN/cm$^2$ (hereinafter referred to as T2) is measured as follows. Measurement is made with a tensile-compression tester RTM-100, supplied by Toyo Baldwin Co., Ltd., which is capable of deforming a test piece by compressing at a constant speed. A square piece of 50 mm by 50 mm cut out of the bulky sheet material 10 is set on the tester, and a compression plate fitted to a load cell (rating: 5 kg) is moved downward at a rate of 10 mm/min to compress the test piece. T2 is obtained from the displacement by compression under a load imposed to the load cell. Specifically, the position of the compression plate giving a reading of 2 gf (0.1% of the full scale, 2 kg) is taken as an original point, and a displacement X1 under a pressure of 0.4 cN/cm$^2$ and a displacement X2 under a pressure of 34.2 cN/cm$^2$ are read. T2 is calculated from X1, X2, and T1 according to equation (1). It should be noted that the values of X1 and X2 are negative with the value of the original point being set to zero.

$$T2=T1+(X2-X1) \quad (1)$$

It is preferred that the bulky sheet material 10 have a compressive deformation percentage of 30 to 85%, particularly 40 to 70%, the compressive deformation percentage being calculated from T1 and T2 by equation (2):

$$\text{Compressive deformation (\%)} = (T1-T2)/T1 \times 100 \quad (2)$$

The bulky sheet material 10 having such a compressive deformation percentage exhibits improved deformability in conformity to a wearer's contour or movement when used as an element constituting an absorbent article.

In order for the bulky sheet material 10 to have sufficient compressive deformability and bulkiness, it is preferred for the bulky sheet material 10 to have a basis weight of 20 to 200 g/m$^2$, particularly 40 to 150 g/m$^2$. The basis weight is obtained by weighing a cut piece of the bulky sheet material 10 having a size of 50 mm by 50 mm or larger by means of an electronic balance whose figure of merit is 1 mg and calculating the weight per m$^2$.

The second layer 2 of the bulky sheet material 10 is made up of a material showing an elastomeric behavior. When extended in the planar direction, the second layer 2 exerts a prescribed shrinkage stress. The bulky sheet material 10 as a whole exhibits an elastomeric behavior and extensibility. Thus, where used as an element constituting an absorbent article, the bulky sheet material 10 follows the movement of a wearer to give a good fit and prevent leaks. It does not matter whether the first layer 1 exhibits an elastomeric behavior provided that it is extensible.

It is preferred that the bulky sheet material 10 preferably has a recovery of 50% or more, more particularly 60% or more, still particularly 60 to 90%, from 50% extension so as to exhibit sufficient elastomeric behavior (the recovery at 50% extension will be referred simply to extension recovery). While an extension recovery sometimes varies according to the direction of extension, e.g., machine direction and cross direction, sufficient elastomeric behavior is manifested as long as the extension recovery falls within the above range in at least one arbitrary direction.

The extension recovery is measured as follows. The tensile-compression tester RTM-100, supplied by Toyo Baldwin, is used in a tensile mode. A square specimen of 50 mm by 50 mm cut out of the bulky sheet material 10 is set between air chucks at an original chuck-to-chuck distance of 30 mm. The chuck that is attached to the load cell (rating: 5 kg) is lifted at a speed of 100 mm/min to extend the specimen. When the specimen is extended 50%, i.e., when the chuck distance reaches 45 mm, the moving direction of the chuck is reversed, and the chuck is moved downward at a speed of 100 mm/min to the original position. Meantime, the load detected from the load cell is recorded against the extension of the specimen. The extension recovery can be obtained from equation (3):

$$\text{Extension recovery} = \text{recovery length/maximum extension } (=15 \text{ mm}) \quad (3)$$

wherein "recovery length" is the distance the chuck has moved downward from the position of the maximum extension (=15 mm) until the load cell first gives a reading of zero.

As previously stated, since both the first layer and the second layer are made of a fiber aggregate, the bulky sheet material 10 has breathability as a whole. Preferred breathability of the bulky sheet material 10 is, in term of a Gurley air permeability, 0.6 sec/100 ml or less, particularly 0.4 sec/100 ml or less for securing sufficient breathability, as measured in accordance with JIS P8117. A preferred lower limit of the Gurley air permeability depends on the use of the bulky sheet material 10. For example, for use as a topsheet or a side cuff of an absorbent article, it is about 0.3 s/100 ml. Expressed in terms of KES air permeability measured with a KES-F8 air permeability tester, preferred breathability of the bulky sheet material 10 is 4 kPa·sec/m or less, particularly 3 kPa·sec/m or less for the same reason.

The fibers which constitute the first and second layers will be described. The fiber which constitutes the first layer is suitably one made of a thermoplastic polymer. The thermoplastic polymer includes polyolefins, such as polyethylene and polypropylene; polyesters, such as polyethylene terephthalate; and polyamides. Core/sheath type conjugate fibers or side-by-side type conjugate fibers composed of a combination of these thermoplastic polymers are also useful. The fiber constituting the first layer 1 shows substantially no thermal shrinkage or does not shrink at or below the thermal shrinkage temperature of the fiber constituting the second layer hereinafter described. A preferred fineness of the fiber of the first layer is, while varying depending on the use, 0.5 to 20 dtex, particularly 1.0 to 10 dtex, in view of ease of fiber making. For use as a constituent element of an absorbent article, this fineness is also favorable for feel.

The fiber constituting the second layer is made of thermoplastic polymers that exhibit heat shrinking properties and elastomeric behavior. Such fibers include latent crimping fibers which can be handled similarly to conventional fibers for nonwoven application and, when heated to a prescribed temperature, develop helical crimp and thus shrink. Latent crimping fibers are capable of developing heat shrinking properties and elastomeric behavior simultaneously.

The latent crimping fibers include conjugate fibers having an eccentric core/sheath configuration or a side-by-side configuration and comprising two thermoplastic polymers different in shrinkage. Useful examples are described in JP-A-9-296325 and Japanese Patent 2759331.

The first layer and the second layer can further comprise other fibers, for example water-absorbing fibers such as rayon, cotton, and hydrophilic acrylic fiber.

The forms of the fiber aggregate as a first layer include a web as formed by carding (defined later more specifically), nonwoven fabric formed by thermal bonding, nonwoven fabric formed by water needling, nonwoven fabric formed by needle punching, nonwoven fabric formed by solvent bonding, nonwoven fabric formed by spun bonding, nonwoven fabric formed by melt blowing, and knitted fabric. On shrinkage of the second layer, a web formed by carding forms bulky protrusions filled with the fibers with the fibers orientated along the protruded contour, while nonwoven fabric or knitted fabric forms hollow dome-shaped protrusions. In particular, a web formed by carding becomes a very sparse first layer to provide a bulky sheet material which is capable of transporting and retaining highly viscous fluids and exhibits high compressive deformability when compressed in the thickness direction. The highly viscous fluids as referred to herein include soft tools, menstrual blood, cleaning agents or humectants for human bodies, and cleaning agents for objects.

The web formed by carding is a fiber aggregate before being fabricated into nonwoven fabric. That is, the fibers constituting the carded web are in a very loosely entangled state before being subjected to post-treatment for producing nonwoven fabric, such as thermal bonding by an air-through method or a calendering method. The carded web as a first layer is joined with a second layer and, either after or simultaneously with the joining, the fibers of the web are bonded together or mechanically entangled by thermal bonding or with a solvent.

The form of the fiber aggregate as a second layer includes (1) a web as formed by carding which contains latent crimping fibers, (2) thermally shrinkable nonwoven fabrics formed by thermal bonding, water needling, needle punching, solvent adhesion, spun bonding, or melt blowing, and (3) thermally shrinkable net. The term "thermally shrinkable nonwoven fabric" is used to describe nonwoven fabric having the property of shrinking on heating to a prescribed temperature.

While depending on the use of the bulky sheet material 10, it is preferred for the first layer to have a basis weight of 5 to 50 g/m², particularly 15 to 30 g/m², to exhibit sufficient bulkiness and improved compressive deformability which leads to improved flexibility. While depending on the use of the bulky sheet material 10, it is preferred for the second layer to have a basis weight of 5 to 50 g/m², particularly 15 to 30 g/m², for the same reasons as for the first layer and, in addition, to ensure sufficient breathability. The term "basis weight" as used with respect to the first and the second layers denotes the respective basis weights before the first and the second layers are joined to form a bulky sheet material 10.

Either one of the first and the second layers may be perforated to improve permeability to wastes such as urine, blood and soft tools and to reduce leakage and overhydration when the bulky sheet material 10 is used as, for example, a topsheet of an absorbent article. Both the first and the second layers can be perforated. In this case, the positions of the perforations may be either the same or different between the first and the second layers.

The perforations (openings) preferably have a diameter of 0.2 to 10 mm from the standpoint of liquid permeability and feel. The perforations are preferably distributed uniformly over the entire area of the bulky sheet material 10. For liquid permeability and feel, the perforations are preferably put at an interval of 0.5 to 20 mm.

Methods of producing the bulky sheet material 10 preferably include the following methods (1) and (2).

Method (1):
A second layer that is a fiber aggregate comprising fibers which are made of a thermoplastic polymer and exhibit thermal shrinkability and elastomeric behavior and a first layer that is a fiber aggregate comprising fibers which are made of a thermoplastic polymer and show substantially no thermal shrinkage or do not shrink at or below the thermal shrinkage temperature of the fibers constituting the second layer are superposed on each other and joined together in parts in a prescribed pattern. A web formed by carding is preferably used as a first layer for the reasons described previously. The joined sheets are heat treated at or above a temperature at which thermal shrinkage of the fibers constituting the second layer is initiated, whereby the second layer shrinks. It follows that the portions of the first layer surrounded by the joints are raised to form a three-dimensional configuration. The thermal shrinkage of the second layer preferably ranges from 20 to 90%, particularly 40 to 80%, from the viewpoint of thermal shrinkage controllability, extension recovery and compressive deformability of the resulting bulky sheet material, and bulkiness developed by the raised portions. The heat shrinkage is an area shrinkage percentage obtained from the original area $S_0$ before shrinkage and the area $S_1$ after shrinkage according to equation (4):

$$\text{Shrinkage}(\%) = (S_0 - S_1)/S_0 \times 100 \quad (4)$$

The second layer can be shrunken by use of, for example, a desk type constant temperature dryer or an air-through heat treating machine used in the production of thermally bonded nonwoven fabric.

Where the second layer displays elastomeric behavior before being joined with the first layer, the following method (2) can be adopted.

Method (2):
The first layer and the second layer are joined in parts in a prescribed pattern with the second layer being in an extended state. On releasing the second layer from extension, the portions of the first layer surrounded by the joints are raised to form a three-dimensional configuration.

Figure 5:
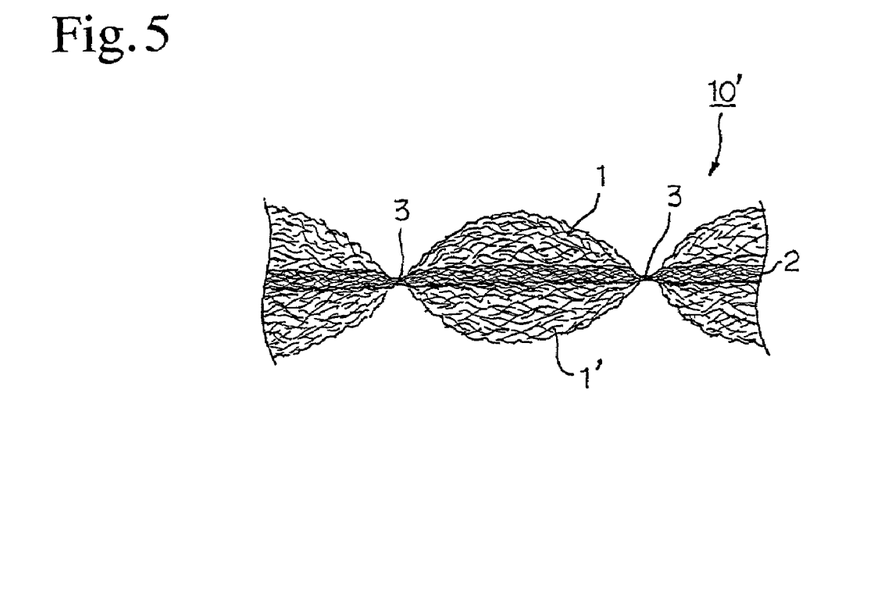
FIG. 5 is a cross-section of a bulky sheet material according to yet another embodiment of the present invention, which corresponds to FIG. 2.

It should be understood that the present invention is not limited to the aforementioned specific embodiments. For example, the bulky sheet material may have provided on the second layer 2 thereof a third layer, which may be the same or different from the first layer 1, to have a three-layer structure. An example of the three-layer structure is shown in FIG. 5, in which a bulky sheet material 10' has a second layer 2, a first layer 1 provided on one side of the second layer 2, and a third layer 1' provided on the other side of the second layer 2. Both the first layer 1 and the third layer 1' are raised in the portions surrounded by joints 3 to form three-dimensional protrusions.

The first layer 1 and the second layer 2 can be made of materials substantially permeable to air other than the above-described fiber aggregates. For example, air-permeable films, perforated films, nets, composites of two or more of these materials or composites of at least one of these materials and a fiber aggregate can be used.

A fiber aggregate comprising elastomer fibers, an elastomer film or an elastomer net is also serviceable as a second layer 2. The bulky sheet material having a second layer 2 made of these materials is prepared by the above-described method (2). Elastomers which can be used as a second layer include natural rubber, isoprene rubber, butadiene rubber, 1,2-polybutadiene, styrene-butadiene rubber, chloroprene rubber, nitrile rubber, butyl rubber, ethylene-propylene rubber, urethane rubber, and various rubbers known as thermoplastic elastomers, such as those having a urethane type, styrene type, ester type, olefin type or amide type hard segment, and ethylene-α-olefin copolymers obtained by using a metallocene catalyst.

The bulky sheet material of the present invention is suited for use as an element constituting disposable articles which are disposed of after used once or several times. It is particularly useful as a constituent element of disposable absorbent articles, such as sanitary napkins and disposable diapers, or disposable cleaning wipers for objects or human bodies. Where applied to a disposable absorbent article, for example, an absorbent article comprising a liquid-permeable topsheet, a liquid-impermeable backsheet, and an absorbent member interposed therebetween, the bulky sheet material is used as part of the topsheet, the backsheet or the side cuffs.

The present invention will now be illustrated in greater detail with reference to Examples. The following Examples are presented as being exemplary of the present invention and should not be considered as limiting.

EXAMPLE 1

(1) Preparation of First Layer

Core/sheath conjugate fiber NBF (SH) (available from Daiwabo Co., Ltd.; 2.2 dtex×51 mm; core: polyethylene terephthalate; sheath: polyethylene) was carded into a web having a basis weight of 30 g/m$^2$, which was used as a first layer.

(2) Preparation of Second Layer

Latent crimping fiber CPP (available from Daiwabo Co., Ltd.; 2.2 dtex×51 mm) was carded into a web having a basis weight of 35 g/m$^2$, which was used as a second layer.

(3) Preparation of Bulky Sheet Material

Figure 6:
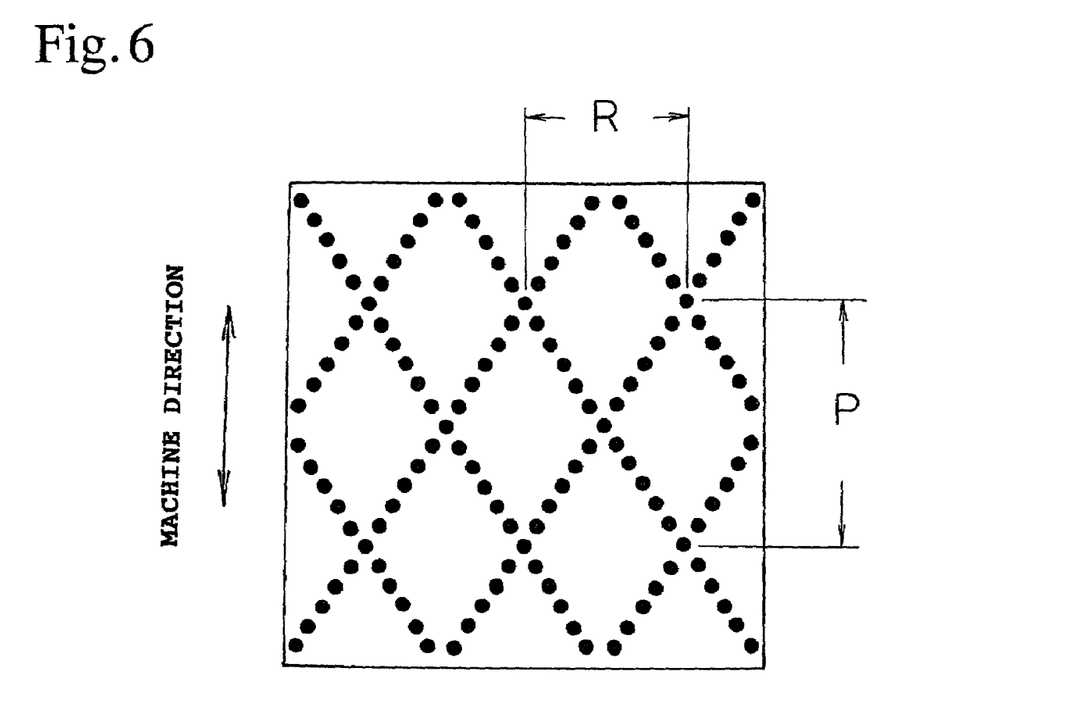
FIG. 6 shows a pattern of joints.

The first layer and the second layer were superposed on each other and joined in parts by ultrasonic embossing. Joints formed by the embossing each had a circular shape and were arranged to form a rhombic lattice pattern as shown in FIG. 1. The joined layers were passed through hot air at 130° C.±10° C. for 5 to 10 seconds to crimp the latent crimping fibers. As a result, the second layer shrank, and the first layer was raised in the portions surrounded by the joints to obtain a bulky sheet material having a great number of protrusions shown in FIG. 1. The individual protrusions were filled with fibers of the first layer as shown in FIG. 2. The area ratio of the joints was 7.3%. The specific pattern of the joints are shown in FIG. 6. Small circles of the joints are arranged to form a rhombic lattice pattern. Each joint, which was a small circle, had a diameter of about 2 mm. Each diamond formed of the lines of joints had a longer diagonal P of 39.3 mm and a shorter diagonal R of 24.2 mm. The thermal shrink of the second layer was carried out by use of a desk type constant temperature dryer or an air-through heat treating machine used in the production of thermally bonded nonwoven fabric. The temperature (130±10° C.) of hot air used in thermal shrink is the initial temperature of hot air before being applied to the sheet, i.e., the initial temperature detected by a temperature sensor set near the air plenum (hereinafter the same). The term "initial temperature" means the temperature in the constant temperature dryer immediately before the sheet is introduced therein or the temperature in the heat treating machine immediately before the sheet is introduced therein.

EXAMPLE 2

A bulky sheet material was prepared in the same manner as in Example 1, except that the web as a first layer was fabricated of core/sheath conjugate fiber NBF (SH) (available from Daiwabo Co., Ltd.; 11 dtex×51 mm) and had a basis weight of 30 g/m$^2$.

EXAMPLE 3

(1) Preparation of First Layer

Spun-bonded nonwoven fabric PS104 (available from Mitsui Chemicals, Inc.; main component: polypropylene; basis weight: 20 g/m$^2$) was used as a first layer.

(2) Preparation of Second Layer

A second layer was prepared in the same manner as in Example 1.

(3) Preparation of Bulky Sheet Material

Figure 3B:
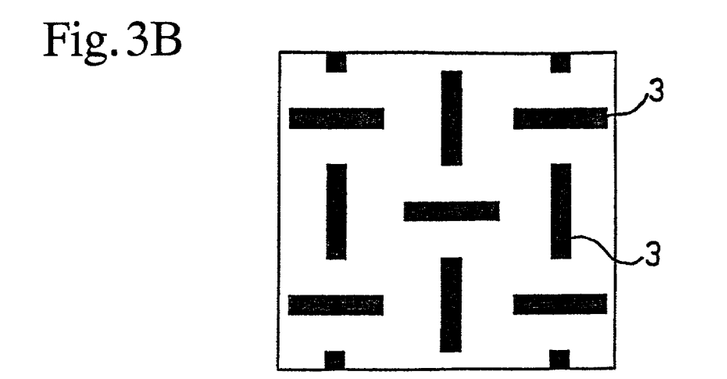
FIG. 3B is a partial enlarged view of the bulky sheet material shown in FIG. 3A.

The first layer and the second layer were superposed on each other and joined by the same manner as in Example 1. Joints formed are shown in FIG. 3B. The bulky sheet material thus obtained has a great number of wrinkly protrusions. The individual protrusions were hollow.

Comparative Example 1

Spun-bonded nonwoven fabric P03020 (available from Asahi Chemical Industry Co., Ltd.; main component: polypropylene; basis weight: 20 g/m$^2$) was used as a comparative sheet.

Comparative Example 2

PET spun-laced nonwoven fabric Sontara 8000 (available from E. I. du Pont de Nemours and Company; basis weight: 41 g/m$^2$) was used as a comparative sheet.

Comparative Example 3

Spun-bonded nonwoven fabric PS-120 (available from Mitsui Chemicals, Inc.; 100% made of polypropylene; basis weight: 100 g/m$^2$) was used as a comparative sheet.

Comparative Example 4

(1) Preparation of First Layer

Spun-bonded nonwoven fabric PS-104 (available from Mitsui Chemicals, Inc.; basis weight: 20 g/m$^2$) comprising predominantly polypropylene was used as a first layer.

(2) Preparation of Second Layer

Thermally shrinkable fiber PNE (available from Daiwabo Co., Ltd.; 2.2 dtex×51 mm) was carded into a web having a basis weight of 35 g/m$^2$, which was used as a second layer.

(3) Preparation of Bulky Sheet Material

A bulky sheet material was prepared from the above-described first and second layers in the same manner as in Example 1, provided that the joints formed by the ultrasonic embossing were arranged to form a pattern as shown in FIG. 3. The area ratio of the joints was 24.8%.

Performance Evaluation:

The basis weight, thickness (under a pressure of 0.4 cN/cm$^2$ or 34.2 cN/cm$^2$), thickness of the joints, compressive deformation (%), apparent density (under a pressure of 0.4 cN/cm$^2$ or 34.2 cN/cm$^2$), extension recovery in the machine direction (MD) and the cross direction (CD), and KES air permeability of the sheet prepared in Examples and Comparative Examples were measured. The results obtained are shown in Table 1 below. The thermal shrinkages (%) in the preparation of the sheet materials are also shown. The term "machine direction (MD)" is the direction of sheet running on the sheeting machines. The extension recovery (at 50% extension) in MD is an extension recovery measured on a test specimen set with its MD agreeing with the traveling direction of the chuck. The term "cross direction (CD)" is the direction perpendicular to MD. The extension recovery in CD is an extension recovery measured on a test specimen set with its CD agreeing with the traveling direction of the chuck.

The sheets were also evaluated for conformability to a contour and movement in accordance with the following method. The results obtained are shown in Table 1.

Conformability to Contour and Movement:

Sanitary napkins were prepared by using the sheet as a topsheet. A panel of 5 members touched the topsheet and scoured in terms of conformability to the contour of their hands according to the following scoring system. Further, the sheet was cut to a size of 100 mm by 200 mm to prepare a cleaning wiper for objects and human bodies. A panel of 5 members wiped a table and a human body with the cleaning wiper and scored in conformability to their hands and to the table and the human body according to the same scouring system. The sores by 5 panel members were added up and divided by 5 to give an average.

| Scouring system: | |
|---|---|
| Satisfactory | 5 points |
| Slightly satisfactory | 4 points |
| Medium | 3 points |
| Slightly poor | 2 points |
| Poor | 1 point |

TABLE 1

| | | Example No. | | | Comparative Example No. | | | |
|---|---|---|---|---|---|---|---|---|
| | | 1 | 2 | 3 | 1 | 2 | 3 | 4 |
| Thermal shrinkage (%) | | 70-80 | 70-80 | 70-80 | — | — | — | 70-80 |
| Basis weight (g/m²) | | 174.0 | 115.9 | 136.7 | 20 | 41 | 100 | 112.2 |
| Thickness (mm) | 0.4 cN/cm² | 7.49 | 5.77 | 6.63 | 0.27 | 0.44 | 0.64 | 3.09 |
| | 34.2 cN/cm² | 2.00 | 1.67 | 2.48 | 0.15 | 0.25 | 0.49 | 0.90 |
| Thickness of joints (mm) | | 0.58 | 0.48 | 0.51 | — | — | — | 0.48 |
| Compressive deformation (%) | | 73.2 | 71.1 | 62.7 | 44.2 | 43.2 | 23.4 | 0.5 |
| Apparent | 0.4 cN/cm² | 23.2 | 20.1 | 20.6 | 87.8 | 80.9 | 151.9 | 36.3 |
| density (kg/m³) | 34.2 cN/cm² | 87.1 | 69.7 | 55.2 | 158.0 | 142.4 | 198.4 | 124.7 |
| Extension | MD | 78.0 | 72.0 | 76.0 | broken | broken | broken | 39.3 |
| Recovery (%) | CD | 78.0 | 68.0 | 74.0 | 35.0 | 12.0 | broken | 49.5 |
| KES air permeability (kPa · s/m) | | 0.039 | 0.029 | 0.039 | 0.017 | 0.034 | 0.262 | 0.041 |
| Conformability to contour and movement (points) | | 4.8 | 4.0 | 4.6 | 2.4 | 2.8 | 1.2 | 2.8 |

The bulky sheet materials of Examples are twice or more as thick as the comparative sheet materials. It is understood that the bulkiness of the sheet materials of the present invention cannot be achieved by conventional sheet materials. The apparent densities of the bulky sheet materials of Examples are half or less of those of the comparative sheet materials, indicating the low-density structure of the bulky sheet materials of the invention compared with the conventional sheet materials. The sheet materials of Examples show 60% or more recovery from 50% extension in both MD and CD, while the comparative sheet materials are broken or has an extension recovery of not more than 50%, proving that the sheet materials of Examples exhibit high recovery from extension. The sheet materials of Examples exhibit satisfactory conformability and high recovery from deformation compared with the comparative sheet materials.

Having been described in detail, the bulky sheet material according to the present invention exhibits sufficient recovery when extended in the planar direction and sufficient compressive deformability when compressed in the thickness direction. The bulky sheet material of the present invention is particularly suited for use as a constituent element of disposable absorbent articles.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2000-311415 filed Oct. 12, 2000, which is incorporated herein by reference.

What is claimed is:

1. A bulky sheet material having three-dimensional protrusions comprising a first layer and a second layer adjacent to the first layer, said first layer and said second layer being partly joined together at joints in a prescribed pattern, said first layer having a number of said protrusions which are located between said joints, said second layer comprising a material which exhibits elastomeric behavior, and said bulky sheet material exhibiting elastomeric behavior as a whole and breathability and has a recovery of 60% or more from 50% extension, and wherein said second layer comprises a web formed by carding comprising latent crimping fibers having a helical shape which are made of a thermoplastic polymer having an eccentric core-sheath or side-by-side configuration and comprising two thermoplastic polymers different in shrinkage and exhibit both thermal shrinkability and elastomeric behavior, and said first layer comprises a fiber aggregate comprising fibers which are made of a thermoplastic polymer and have substantially no thermal shrinkability or do not shrink at or below the thermal shrinkage temperature of said fibers exhibiting thermal shrinkability, said three-dimensional protrusions comprised of fiber-filled protrusions, and said sheet material having been heat-treated at or above a temperature at which thermal shrinkage of the fibers constituting the second layer is initiated, whereby said second layer shrinks to form said protrusions in said first layer, and wherein the ratio T/T' of the thickness T of the bulky sheet material measured at the protrusions to the thickness T' of the bulky sheet material measured at the joints is at least 2, wherein the thickness T is measured under a pressure of 0.4cN/cm², and the thickness T' is measured under a pressure of 10 to 40 N/cm² applied to the joint, and wherein the thickness T ranges from 1.5 to 10 mm measured under a pressure of 0.4 cN/cm².

2. The bulky sheet material according to claim 1, which has a basis weight of 20 to 200 g/m², apparent density of 5 to 50 kg/m³ under a pressure of 0.4 cN/cm², and an apparent density of 20 to 130 kg/m³ under a pressure of 34.2 cN/cm².

3. The bulky sheet material according to claim 1, wherein at least one of said first layer and said second layer has a large number of perforations.

4. An absorbent article comprised of a liquid-permeable topsheet, a liquid-impermeable backsheet and an absorbent member interposed between said topsheet and said backsheet, wherein at least one of said topsheet, backsheet or absorbent member of said absorbent article is comprised of a bulky sheet material having three-dimensional protrusions comprising a first layer and a second layer adjacent to the first layer, said first layer and said second layer being partly joined together at joints in a prescribed pattern, said first layer having a number of said protrusions which are located between said joints, said second layer comprising a material which exhibits elastomeric behavior, and said bulky sheet material exhibiting elastomeric behavior as a whole and breathability and has a recovery of 60% or more from 50% extension, and wherein said second layer comprises a web formed by carding comprising latent crimping fibers having a helical crimp which are made of a thermoplastic polymer having an eccentric core/sheath or side-by-side configuration and comprising two thermoplastic polymers different in shrinkage and exhibit both thermal shrinkability and elastomeric behavior, and said first layer comprises a fiber aggregate comprising fibers which are made of a thermoplastic polymer and have substantially no thermal shrinkability or do not shrink at or below the thermal shrinkage temperature of said fibers exhibiting thermal shrinkability, said three-dimensional protrusions comprised of fiber-filled protrusions, and said sheet material having been heat-treated at or above a temperature at which thermal shrinkage of the fibers constituting the second layer is initiated, whereby said second layer shrinks to form said protrusions in said first layer, and wherein the ratio T/T' of the thickness T of the bulky sheet material measured at the protrusions to the thickness T' of the bulky sheet material measured at the joints is at least 2, wherein the thickness T is measured under a pressure of 0.4 $cN/cm^2$, and the thickness T' is measured under a pressure of 10 to 40 $N/cm^2$ applied to the joint, and wherein the thickness T ranges from 1.5 to 10 mm measured under a pressure of 0.4 $cN/cm^2$.

5. The bulky sheet material of claim 1, wherein said fiber aggregate of said first layer is selected from the group consisting of a carded web, a nonwoven fabric, and a knitted fabric.

6. The absorbent article of claim 4, wherein at least one of said topsheet or backsheet is comprised of said bulky sheet material.

7. The absorbent article of claim 4, wherein at least said topsheet is comprised of said bulky sheet material.

8. The absorbent article of claim 4, wherein said fiber aggregate of said first layer is selected from the group consisting of a carded web, a nonwoven fabric, and a knitted fabric.

9. The absorbent article of claim 4, wherein said article is a sanitary napkin.

10. The bulky sheet material according to claim 1, wherein said sheet material has a breathability in terms of Gurley air permeability of 0.6 sec/100 ml or less as measured in accordance with JIS P8117.

11. The absorbent article according to claim 4, wherein said bulky sheet material has a breathability in terms of Gurley air permeability of 0.6 sec/100 ml or less as measured in accordance with JIS P8117.

12. The absorbent article according to claim 4, wherein said bulky sheet material has a basis weight of 20 to 200 $g/m^2$, an apparent density of 5 to 50 $kg/m^3$ under a pressure of 0.4 $cN/cm^2$, and an apparent density of 20 to 130 $kg/m^3$ under a pressure of 34.2 $cN/cm^2$.

13. The absorbent article according to claim 4, wherein at least one of said first layer and said second layer has a large number of perforations.

14. The bulky sheet material according to claim 1, wherein the ratio T/T' ranges from 2 to 6.

15. The absorbent article according to claim 4, wherein the ratio T/T' ranges from 2 to 6.

* * * * *